United States Patent [19]

Neufeld

[11] 3,955,568

[45] May 11, 1976

[54] TOOL AND METHOD FOR USE IN TOTAL HIP IMPLANT

[76] Inventor: Alonzo J. Neufeld, 1650 Parway Drive, Glendale, Calif. 91206

[22] Filed: Apr. 17, 1975

[21] Appl. No.: 569,053

[52] U.S. Cl. .................................... 128/92 E; 3/1
[51] Int. Cl.² ............................................ A61F 5/04
[58] Field of Search............ 128/92 E, 92 C, 92 CA, 128/92 R, 92 EC, 92 F, 92 G, 83; 3/1

[56] References Cited
UNITED STATES PATENTS

| | | | |
|---|---|---|---|
| 3,585,994 | 6/1971 | Huggler et al. ........................ | 128/83 |
| 3,801,989 | 4/1974 | McKee............................ | 128/92 CA |
| 3,818,514 | 6/1974 | Clark.............................. | 128/92 CA |

Primary Examiner—John D. Yasko
Attorney, Agent, or Firm—Huebner & Worrel

[57] ABSTRACT

A tool for inserting a prosthetic femoral head into and for removing it from a prosthetic hip socket, the tool including a handle, means for engaging a prosthetic femoral head and neck therebelow and a rod connecting the handle with the engaging means.

A method of inserting a prosthetic femoral head into and removing it from a prosthetic hip socket in which the femoral head and its neck below are engaged with a twistable tool, followed by twisting the outer end of the tool and twisting the femoral head so as to move it transversely into or out of the hip socket.

10 Claims, 4 Drawing Figures

U.S. Patent May 11, 1976 3,955,568
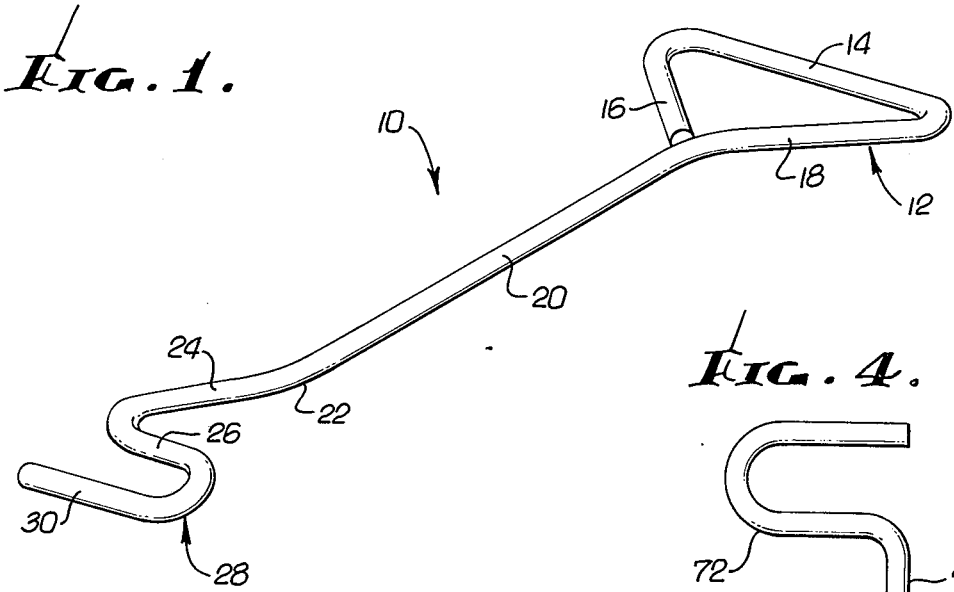
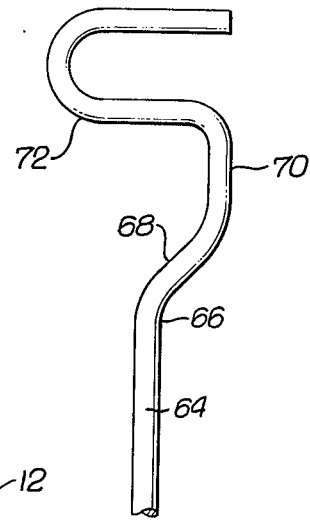
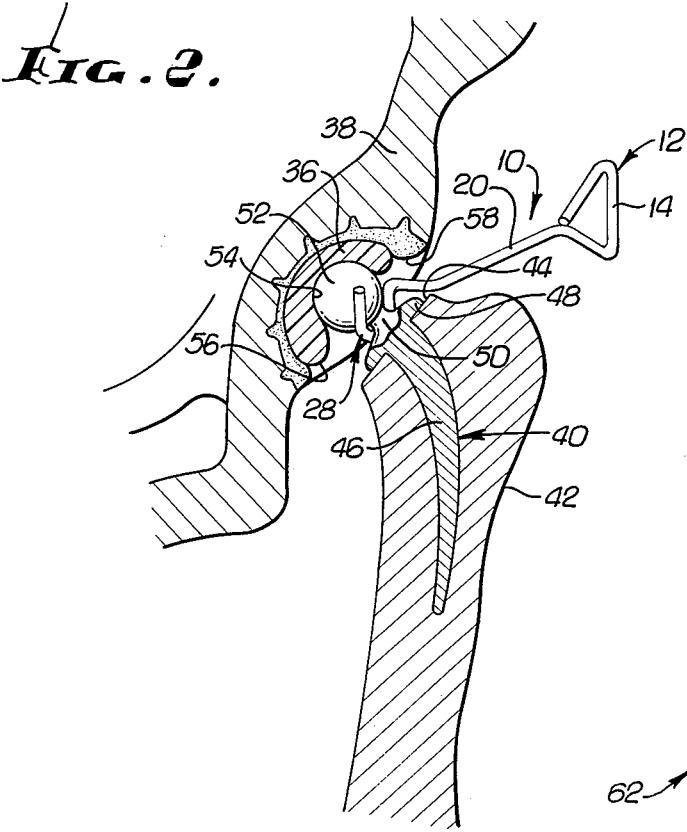
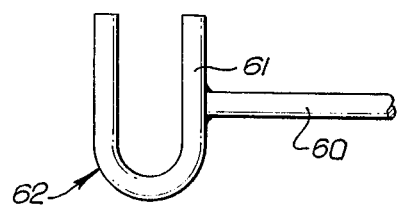

TOOL AND METHOD FOR USE IN TOTAL HIP IMPLANT

BACKGROUND OF THE INVENTION

The present invention relates to a tool and method for use in total hip implant surgery by which the head of a prosthetic femoral device may be twisted into and out of a prosthetic hip socket. When a total prosthetic hip is implanted in a patient, the femoral head or ball must be made to fit perfectly within the socket so as to not cause the patient problems thereafter. That is, the head must be fitted so as to move easily in the socket, but neither be too loose nor too tight.

During the surgery, which requires an incision of approximately 8 inches in length, a prosthetic socket is fitted and secured in the area of the natural socket in the pubis, and after the natural head has been removed from the femur, a trial prosthetic device is inserted into the femur for trial fitting of its head into the socket. Such trials are necessary to accomplish the proper fit of the head within the socket. Because the prosthetic femoral heads are made of metal, ground to be extremely smooth and are easily scored, the trial fittings are accomplished with prosthetic devices having plastic heads to avoid damaging the actual head to be used.

In these trial fittings and in the final fitting, it is very difficult to insert each femoral head into the implanted socket, and to remove it therefrom, because of the tight fitting of the natural hip and natural femur and which will exist after the operation is completed between the prosthetic hip socket and the prosthetic femoral device.

In the prior art there has been no satisfactory means or tool for accomplishing relatively easy insertion and removal of the femoral heads from the implanted socket. Generally, the femoral head was moved into the socket with great effort and pulled out of the socket with great effort by an ordinary hook-shaped tool. This inadequate phase of the total implant surgery had existed for years prior to the present invention.

SUMMARY OF THE INVENTION

The present invention is used by having one end thereof engaged with the neck of a prosthetic femoral implant just below the head and by which the prosthetic device is twisted so that the head may be relatively easily inserted into or removed from the prosthetic socket.

Accordingly, it is an object of the present invention to provide an improved tool and method for use in total hip implant surgery.

It is another object of the invention to provide a tool for use in total hip implant surgery which is operated by a simple twisting action to insert femoral devices into and remove them from the implanted socket.

Further objects and advantages of the invention may be brought out in the following part of the specification wherein small details have been described for the competence of disclosure, without intending to limit the scope of the invention which is set forth in the appended claims.

BRIEF DESCRIPTION OF THE DRAWINGS

Referring to the accompanying drawings, which are for illustrative purposes:

FIG. 1 is a perspective view of the tool according to the invention;

FIG. 2 is a partially cross-sectional view of a total hip implant, illustrating the engagement of the tool with the femoral prosthetic device;

FIG. 3 is a fragmentary view of another embodiment of the invention; and

FIG. 4 is a fragmentary view of still another embodiment of the invention.

DESCRIPTION OF THE PREFERRED EMBODIMENTS

Referring again to the drawings, there is shown a tool, generally designated as 10, for inserting and removing the head of a prosthetic femoral device from a prosthetic hip socket, the tool being typically made from a single metal rod. The tool has a handle 12 formed as an approximate isosceles triangle, having a gripping base 14 and two legs 16 and 18. An intermediate portion or rod 20 extends from the leg 18 in a direction substantially perpendicular to and on an axis that substantially bisects the gripping base 14. At an end 22 of the rod 20 there is an offset portion 24 which joins a proximate leg 26 of a U-shaped member 28 having a distal leg 30, the U-shaped member forming the inner end or engaging portion of the tool.

The legs 26 and 30 are substantially coextensive and substantially parallel to each other and to the gripping base 14 of the handle, so that the axis of the rod portion 20 is substantially perpendicular to and substantially bisects the legs.

In FIG. 2 there is shown a total prosthetic hip implant in which a prosthetic plastic socket member 36 has been secured within a pubis 38 in the place of the natural socket, and in which a prosthetic femoral device, generally designated as 40, has been fitted into the femur 42 after the natural femoral ball or head has been cut off along the surface 44.

The prosthetic femoral device is comprised of a stem 46 inserted into the femur, a shoulder 48 supported on the cut surface 44, a neck 50, and a head or ball 52. The socket 36 has a approximately semispherical cavity 54 into which the ball 52 is relatively snugly fitted and has outer annular curved surfaces as at 56 and 58. The tool 10 is shown having its inner U-shaped portion 28 engaged with the neck 50 of the femoral prosthetic device.

During the surgery, after the socket has been implanted, a trial prosthetic femoral device being in the femur, it must be forced into the socket, the forcing being required because of the natural, relatively tight fitting of the femur and the pubis to form the hip joint. To insert the head of the femoral device into the socket, the tool 10 is engaged as shown, and held with the surgeon's hand on the gripping base 14 within or around the triangle, the tool being twisted to force the legs 26 and 30 against the head 52 to twist the device and the femur so that the head slips over the smooth, curved surfaces of the socket implant and into the socket cavity. Similarly, to remove the head from the socket, the tool is twisted in the other direction so that the head snaps out. This twisting action of the tool on the femur and prosthetic device provides a very simple and easy method for inserting and removing the head from the socket.

In FIG. 3 a second embodiment of the invention is shown. This device has the same handle as the tool 10 but has an entirely straight intermediate rod portion 60 which is welded to or threadedly engaged with the proximate U leg 61 of the inner engaging portion 62.

Here, also, the axis of the rod is generally perpendicular to the parallel U legs and is positioned to bisect them so that the twisting force is directly applied to the proper place.

In FIG. 4 a third embodiment is illustrated. Here the straight portion of the intermediate rod 64 terminates in a curve 66 and joins an offset portion 68, which in turn joins a straight portion 70. The portion 70 is connected to the end of the U leg 72. In this embodiment the handle is also the same, the axis of the straight portion 64 being perpendicular to the gripping base 14 and also generally perpendicular to and bisecting the U legs. The embodiments in FIGS. 3 and 4 function in the same way as the embodiment shown in FIG. 1.

The invention and its attendant advantages will be understood from the foregoing description and it will be apparent that various changes may be made in the forms, constructions and arrangements of the parts of the invention without departing from the spirit and scope thereof or sacrificing its material advantages, the arrangements hereinbefore described being merely by way of example. I do not wish to be restricted to the specific forms shown or uses mentioned except as defined in the accompanying claims, wherein various portions have been separated for clarity of reading and not for emphasis.

I claim:

1. For use in total hip implant surgery, a tool for inserting a prosthetic femoral head into and for removing from a prosthetic hip socket, comprising:

a handle, an intermediate portion and an inner end portion, means on said inner end portion having two spaced members to engage the neck of the femoral head and to engage the femoral head extending from the femur and for applying a twisting motion to the head and femur, the intermediate portion connecting the handle and the inner end portion and extending in a direction substantially perpendicular to said two spaced members, said inner end portion being connected to said intermediate portion by a portion offset with respect to said intermediate portion.

2. The invention according to claim 1 in which:

said handle is of triangle shape, the triangle having a gripping base at the outer end, said base being generally perpendicular to the direction of the intermediate portion.

3. The invention according to claim 1 in which:

said intermediate portion is a rod.

4. The invention according to claim 3 in which:

said means on said inner end portion includes a U-shaped member having the legs of the U extending transversely with respect to the intermediate portion, the legs of the U engaging the neck and head during the twisting motion.

5. The invention according to claim 4 in which:

said U-shaped member is connected to said intermediate portion by a portion offset with respect to said rod and joining an end of the proximate U leg.

6. The invention according to claim 4 in which:

said handle, said intermediate portion and said end portion are made of a single piece of rod.

7. The invention according to claim 6 in which:

said handle has a gripping member extending in a direction substantially perpendicular to said intermediate portion, said intermediate portion extending substantially perpendicular to the direction of said U legs of said end portion, and the axis of said intermediate portion substantially bisecting said handle gripping member and said U legs.

8. The invention according to claim 1 in which:

said handle having a gripping member extending in a direction substantially perpendicular to said intermediate portion.

9. The invention according to claim 1 in which:

said means on said inner end portion includes a U-shaped member having the legs of the U extending transversely with respect to the intermediate portion, the legs of the U engaging the neck and head during the twisting motion.

10. In total hip implant surgery, a method of inserting a prosthetic femoral head into and removing it from a prosthetic hip socket, comprising:

engaging the neck of the femoral head and the head with an inner end of an elongated tool, wherein the tool comprises, a handle, an intermediate portion and an inner end portion, means on said inner end portion having two spaced members to engage the neck of the femoral head and to engage the femoral head extending from the femur and for applying a twisting motion to the head and femur, the intermediate portion connecting the handle and the inner end portion and extending in a direction substantially perpendicular to said two spaced members, said inner end portion being connected to said intermediate portion by a portion offset with respect to said intermediate portion, twisting the outer end of the tool, twisting the femoral head and the femur, and moving the head transversely with respect to the socket.

* * * * *